(12) United States Patent
Kreutzberger et al.

(10) Patent No.: US 6,239,281 B1
(45) Date of Patent: May 29, 2001

(54) PROCESS FOR PREPARING CARBAMOYL PYRIDINIUM COMPOUNDS

(75) Inventors: Charles B. Kreutzberger, Pittsburgh; James A. Manner, Monroeville; Wendy E. Wallace, Pittsburgh, all of PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 09/468,019

(22) Filed: Dec. 20, 1999

(51) Int. Cl.$^7$ .................... C07D 213/04; C07D 213/34

(52) U.S. Cl. .................................. 546/323; 546/314

(58) Field of Search ................................ 546/323, 314

(56) References Cited

U.S. PATENT DOCUMENTS 5,559,239 * 9/1996 Vacca et al. ..................... 546/323

* cited by examiner

*Primary Examiner*—Charanjit S. Aulakh
(74) *Attorney, Agent, or Firm*—Carol A. Marmo; William C. Mitchell

(57) ABSTRACT

Novel process for preparing carbamoyl pyridinium compounds using novel solvent/fatty amine reaction systems.

25 Claims, No Drawings

PROCESS FOR PREPARING CARBAMOYL PYRIDINIUM COMPOUNDS

FIELD OF THE INVENTION

The present invention relates to an improved process for preparing carbamoyl pyridinium compounds using novel solvent/fatty amine reaction system.

BACKGROUND OF THE INVENTION

The use of carbamoyl pyridinium compounds as cross-linking agents in photographic applications is known. See, for example, U.S. Pat. No. 4,063,952, which discloses carbamoyl pyridinium compounds having pyridine rings which carry a sulfo or sulfoalkyl group. According to the '952 method, the alkali metal salt of a starting pyridine compound is reacted with a carbamoyl halide in the presence of a solvent mixture comprising dimethylformamide and methanol, and the reaction product is actively precipitated by the addition of ethyl ether. The alkali metal halide by-product of this reaction precipitates with the desired carbamoyl pyridinium compound.

The carbamoyl pyridinium compounds of the '952 patent are described by the formula:

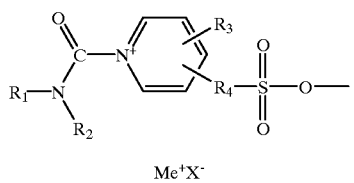

Me$^+$X$^-$ wherein:

$R_1$ and $R_2$ each represents an alkyl group, an aryl group, or an aralkyl group, or $R_1$ and $R_2$ together represent the groups required to complete a piperidine or a morpholine ring;

$R_3$ represents hydrogen, methyl or ethyl;

$R_4$ represents methylene, ethylene, propylene or a single chemical bond;

Me$^+$ represents an alkali metal cation such as Li$^+$, Na$^+$ or K$^+$; and

X$^-$ represents an anion such as Cl$^-$ or Br$^-$.

J01-066,162 also describes the synthesis of carbamoyl pyridinium compounds having a pyridine ring which carries a sulfo or sulfoalkyl group. This process comprises forming the inner salt of a pyridine sulfonic acid in the presence of a tertiary amine and reacting the inner salt with a carbamoyl chloride. By this synthesis, carbamoyl pyridinium compounds free of inorganic salts, e.g., NaCl and KCl, are obtained.

DD 290,879 further describes the synthesis of carbamoyl pyridinium compounds having pyridine rings which carry a sulfo or sulfoalkyl group. This process, which involves reacting a pyridine sulfonic acid with a carbamoyl halide using a nitrile solvent and a tertiary amine, produces a tert-amine hydrochloride by-product. Acetonitrile, propionitrile, butyronitrile and benzonitrile are mentioned as suitable solvents. The object of this process is to provide a nitrile solvent in which the reactants and the tertiary amine hydrochloride by-product are soluble, and the carbamoyl pyridinium compounds are insoluble. It has been found, however, that carbamoyl pyridinium compounds prepared via this process still contain, after the reaction, significant amounts of by-product, which must be eliminated via subsequent washing steps with the nitrile solvent. The yield of the desired carbamoyl pyridinium compound is consequently lowered.

U.S. Pat. No. 5,559,239 discloses a process for preparing carbamoyl pyridinium compounds which involves reacting a pyridine sulfonic acid with a carbamoyl halide in the presence of triethylamine and a ketone (e.g. acetone) solvent. A mixture of the desired carbamoyl pyridinium compound and the tert-amine hydrochloride by-product is recovered from the reaction mixture and the carbamoyl pyridinium compound must then be separated from the by-product using a selective solvent, such as methanol. This second separation step increases the overall process cost and tends to lower yields. It is also believed that methanol washing may be detrimental to product quality.

SUMMARY OF THE INVENTION

The present invention is directed to an improved process for the preparation of carbamoyl pyridinium compounds which comprises reacting a pyridine sulfonic acid with a carbamoyl halide in a by-product solubilizing solvent, such as tetrahydrofuran, methyl t-butyl ether, 1-methyl-2-pyrrolidinone, dimethyl carbonate, dioxane, anisole, dichloroethane, dichloromethane, ethyl acetate, chlorbenzene, toluene or heptane, using a tertiary-amine (e.g. tributylamine) acid scavenger. The tertiary amine hydrohalide by-product formed by this process is solubilized by the chosen solvent, thereby substantially eliminating the need to separate the desired carbamoyl pyridinium from the amine hydrohalide by-product, as described in various prior art processes. Prior art carbamoyl pyridinium/amine hydrohalide separation steps generally remove product, thereby lowering yields.

Thus, the solvent/amine system of the instant process is more efficient in that it generally obviates the dual isolation sequence represented by the process of the '239 patent while providing high yields and purity.

DETAILED DESCRIPTION OF THE INVENTION

Other than in the Examples, or where otherwise indicated, all numbers quantifying ingredients, amounts, dimensions, reaction conditions, etc., used herein are to be understood as modified in all instances by the term 'about'.

The process of the instant invention comprises the steps of:

a) reacting a pyridine sulfonic acid compound with a carbamoyl halide in the presence of an effective amount of a by-product solubilizing solvent and an effective amount of a tertiary amine acid scavenger, thereby forming a reaction product comprising a carbamoyl pyridinium compound, a tertiary amine hydrohalide by-product and said by-product solubilizing solvent, wherein said amine hydrohalide by-product is substantially soluble in said by-product solubilizing solvent and said carbamoyl pyridinium compound is substantially insoluble in said by-product solubilizing solvent; and b) separating said carbamoyl pyridinium compound from said reaction product.

As used herein, the term "by-product solubilizing solvent" means any solvent or solvent composition that is a suitable medium for carrying out the reaction of step a), which has substantial solvating activity towards the tertiary-amine hydrohalide by-product thereby produced, and in which the desired carbamoyl pyridinium compound is substantially insoluble. Solvents believed to be suitable for use in the instant process are selected from the group consisting of: tetrahydrofuran, methyl t-butyl ether, 1-methyl-2-pyrrolidinone, dimethylcarbonate, dioxane, anisole, dichloroethane, dichloromethane, ethyl acetate, chlorobenzene, toluene and heptane. Dichloroethane is a preferred solvent. Due to the solvating characteristics of the instant solvents, separation of the insoluble carbamoyl pyridinium compound from the reaction product can be accomplished in one (1) step via any suitable separation technique, such as filtration or centrifugation.

Optionally, a washing step can be utilized after separation of the carbamoyl pyridinium compound from the reaction product. In this optional step, a washing solvent can be used to prepare a purified final product. This step preferably comprises filter washing the desired carbamoyl pyridinium compound with a washing solvent having solvating activity towards residual reaction impurities, such as unreacted pyridine sulfonic acid and/or tert-amine hydrohalide by-product, but which does not substantially solubilize the desired carbamoyl pyridinium compound. Suitable washing solvents include, but are not limited to, toluene, acetone, isopropyl alcohol, and dichloroethane, with toluene being preferred. An effective amount of washing solvent is used, i.e. that amount necessary to remove impurities from a given carbamoyl pyridinium compound to the desired extent. An effective amount of washing solvent for a given system can be readily determined by a skilled artisan.

Carbamoyl halides useful in the instant process correspond to the following formula:

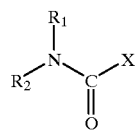

in which:

$R_1$ and $R_2$ (which may be the same or different) each represents an alkyl group having: from 1 to 10 carbon atoms (e.g., methyl, ethyl, 2-ethylhexyl), an aryl group having from 6 to 15 carbon atoms (e.g., phenyl, naphthyl), aralkyl group having from 7 to 15 carbon atoms (e.g., benzyl, phenethyl), or R1 and R2 together form the atoms required to complete a heterocyclic ring (e.g., pyrrolidine, morpholine, piperidine, piperazine, 1,2,3,4-tetrahydroquinoline ring, etc.). X represents an halogen atom (e.g., Cl, Br).

When the term "group" or "ring" is used relative to the present invention, the described chemical material includes the basic group or ring and that group or ring with conventional substituents. Where the term "moiety" is used to describe a chemical compound or substituent, only unsubstituted chemical materials are intended to be included. For example, "alkyl group" includes not only such alkyl moieties as methyl, ethyl, octyl, stearyl, etc., but also such moieties bearing substituent groups such as halogen, cyano, hydroxyl, nitro, amine, carboxylate, etc. On the other hand, "alkyl moiety" includes only methyl, ethyl, octyl, stearyl, cyclohexyl, etc.

Pyridine sulfonic acid compounds useful in this invention correspond to the following general formula:

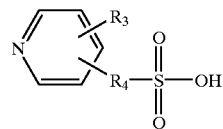

in which:

$R_3$ represents a substituent such as hydrogen, a halogen atom, an alkyl group having from 1 to 10 carbon atoms (e.g., methyl, ethyl), an alkoxy group having from 1 to 10 carbon atoms, a carbamoyl group, or a ureido group. R4 represents an alkylene group having from 1 to 4 carbon atoms (e.g., methylene, ethylene, propylene) or a single chemical bond.

Suitable tertiary amine scavengers useful in the process of present invention correspond to the following general formula:

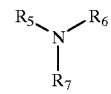

in which:

$R_5$, $R_6$ and $R_7$ (which may be the same or different) each represents an alkyl group having from 2 to 10 carbon atoms. (e.g., ethyl, propyl, butyl, 2-ethylhexyl, etc.), an aryl group having from 6 to 15 carbon atoms (e.g., phenyl, naphthyl), or a cycloalkyl group having from 5 to 8 ring carbon atoms (e.g., cyclohexyl).

Though triethylamine can also be used, higher amines are preferred because the hydrohalides of acid scavengers such as triethylamine generally require more polar solvents for removal, which tends to lower yields and may degrade product quality. The preferred tertiary amine acid scavenger is tributylamine, which, as a fatty amine hydrohalide, is soluble in non-polar solvents and can easily be removed from the reaction media.

As indicated above, suitable solvents useful in the process of the present invention are preferably those in which the reactants (i.e., carbamoyl halides and pyridine sulfonic acids) used, the tertiary amine scavenger used and the tert-amine hydrohalide by-product formed are substantially soluble over the reaction temperature range, and in which the carbamoyl pyridinium compound produced is not soluble. The instant reaction is generally completed in less than ten (10) hours, preferably 2 to 5 hours, at reaction temperatures between 40–80° C., preferably 50–60° C., by adding a stoichiometric quantity of either reactant to a solution comprising the other reactant and effective amounts of the instant by-product solubilizing solvent and a tertiary amine acid scavenger. Effective amounts of these components can be readily determined by a skilled artisan based on stoichiometry and solubilities. At the end of the reaction, the reaction product is preferably cooled to room temperature (i.e., approximately 25° C.) and the desired carbamoyl pyridinium compound is separated from the reaction product, preferably by filtration or centrifugation.

As a subsequent, optional, step in the instant process, the carbamoyl pyridium compound is washed with a suitable solvent to remove residual impurities. Washing can be performed by stirring the separated carbamoyl pyridinium compound in the washing solvent and recovering the relatively insoluble carbamoyl pyridinium compound by filtration or centrifugation. This purification step may be performed one or more times, as necessary. Usually, however, a single wash yields a carbamoyl pyridinium compound product which is substantially devoid of reaction impurities.

The process of the present invention may be effected in a batch or a continuous-type operation. For example, in a batch-type operation, the pyridine sulfonic acid compound used, the tertiary amine acid scavenger used and a quantity of a suitable by-product solubilizing solvent are placed in an appropriate apparatus, such as a jacketed reaction kettle equipped with a stirring mechanism. A stoichiometric quantity of the carbamoyl halide is then added to the reaction mixture, and the mixture is heated to the desired reaction temperature, which is preferably maintained for the duration of the reaction. At the end of the reaction, the carbamoyl pyridinium compound is separated from the reaction product via any suitable separation technique.

It is also contemplated that the preparation of carbamoyl pyridinium compounds via the instant process can be effected in a continuous manner, although not necessarily with equivalent results. For example, when a continuous operation is used, the starting materials can be dissolved in the chosen solvent and fed continuously to a reaction zone maintained at a suitable operating temperature, with stirring. After a desired residence time, the reaction mixture can be continuously discharged to isolate the desired carbamoyl pyridinium compound.

Carbamoyl pyridinium compounds, which can be prepared via the process of the present invention correspond to the general formula:

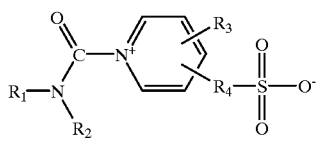

in which $R_1$, $R_2$, $R_3$ and $R_4$ represent substituents as defined for formulas above. Though practical examples of carbamoyl pyridinium compounds which can be prepared using the process of this invention are described at columns 5–7 of U.S. Pat. No. 5,559,239, which columns are hereby incorporated by reference, the present invention is not limited to these compounds.

In a preferred embodiment, the instant invention is directed to a process for preparing 1-[(dimethylamino) carbonyl]-4-(2-sulfoethyl)-hydroxide, inner salt (DMC-PES), via the following reaction:

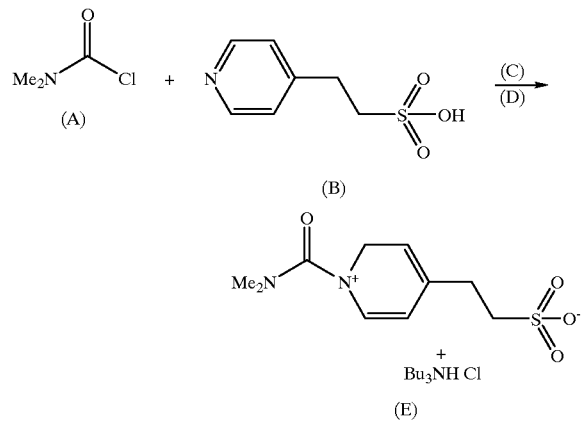

wherein:
(A) is dimethyl carbamoyl chloride (DMCC), $C_3H_6ClNO$ (MW 107.64);
(B) is pyridine ethane sulfonic acid (PESA), $C_7H_9NO_3S$ (MW 108.27);
(C) is a suitable solvent, such as dichloroethane (DCE);
(D) is a suitable tertiary amine, such as tributylamine (TBA), $C_{12}H_{18}N$ (MW 185.36)
(E) is DMC-PES, $C_{10}H_{14}N_2O_4S$ (MW 258.35); and
(F) is tributylamine hydrochloride.

In this process, a stoichiometric amount of DMCC is preferably added to a 40–80° C., preferably 50–60° C., solution of PESA and TBA in DCE; the DCE readily solublizes the amine hydrochloride by-product formed and DMC-PES has very poor solubility in DCE, making it easy to isolate. The mixture is preferably stirred for 2–5 hours, filtered, and optionally, the filterate is washed with hot or cold DCE, or toluene. Shorter reaction times generally tend to increase quantities of unreacted PESA, while longer reaction times generally tend to increase reaction impurities. This reaction generally provides DMC-PES that is greater than 98% pure at yields greater than 90%.

EXAMPLES

The following examples further illustrate the instant process, but are not intended to limit the scope of the present invention in any way.

Examples 1–4

Preparation of DMC-PES

A 500 ml Round bottom Flask fitted with an addition funnel was charged with PESA (50.2 g, 0.268 mol), tributylamine (55.3 g, 0.298 mol), and 200 ml DCE. This slurry was heated to the reaction temperature shown. A 38% w/w solution of DMCC in DCE containing 32.1 g, 0.298 mol of DMCC was then added to the hot solution over the addition time shown. The reaction mixture was aged for 3–4 hours, then filtered hot. The filtrate was then washed with toluene or DCE (2×150 ml) and dried in a vac oven (65° C.@28 inches Hg). The results are shown in Table 1, below:

TABLE 1

| Example No | Reaction Temperature (° C.) | Addition Time (min.) | Age Time (hours) | Wash Solvent | DMC-PES wt % | PESA wt % | Yield % |
| --- | --- | --- | --- | --- | --- | --- | --- |
| 1. | 55 | 20 | 4 | toluene | 98.9 | 0.28 | 93 |
| 2. | 55 | 60 | 4 | toluene | 99.1 | 0.24 | 93 |
| 3. | 55 | 138 | 3 | toluene | 99.7 | 0.22 | 94 |
| 4. | 65–70 | 60 | 4 | DCE | 98.1 | 0.41 | 93 |

We claim:
1. A process for preparing a carbamoyl pyridinium compound, which method comprises:
a) reacting a pyridine sulfonic acid compound with a carbamoyl halide in the presence of an effective amount of a by-product solubilizing solvent and an effective amount of tertiary amine acid scavenger, thereby forming a reaction product comprising a carbamoyl pyridinium compound, a tertiary amine hydrohalide by-product and said by-product solubilizing solvent, wherein said tertiary amine hydrohalide by-product is substantially soluble in said by-product solubilizing solvent and said carbamoyl pyridinium compound is substantially insoluble in said by-product solubilizing solvent; and b) separating said carbamoyl pyridinium compound from said reaction product.

2. The process of claim 1, wherein said by-product solubilizing solvent is selected from the group consisting of tetrahydrofuran, methyl-t-butyl ether, 1-methyl-2-pyrrilidinone, dimethylcarbonate, dioxane, anisole, dichloroethane, dichloromethane, ethyl acetate, chlorobenzene, toluene and heptane.

3. The process of claim 1, wherein said by-product solubilizing solvent is dichlorothane.

4. The process according to claim 1, wherein said carbamoyl halide corresponds to the formula:

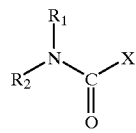

in which
$R_1$ and $R_2$ (which may be the same or different) each represents an alkyl group having from 1 to 10 carbon atoms, an aryl group having from 6 to 15 carbon atoms, an aralkyl group having from 7 to 15 carbon atoms, or R1 and R2 together form the atoms required to complete a heterocyclic ring, and X represents an halogen atom.

5. The process of claim 1, wherein the pyridine sulfonic acid compound corresponds to the formula:

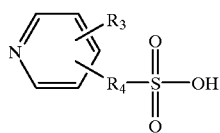

in which:
$R_3$ represents a hydrogen atom, a halogen atom, an alkyl group having from 1 to 10 carbon atoms, an alkoxy group having from 1 to 10 carbon atoms, a carbamoyl group, or a ureido group, and
$R_4$ represents an alkylene group having from 1 to 4 carbon atoms or a single chemical bond between the pyridinium ring and the sulfonic acid moiety.

6. The process of claim 1, wherein the tertiary amine acid scavenger corresponds to the formula:

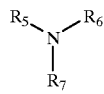

in which:
$R_5$, $R_6$ and $R_7$, which may be the same or different, each represents an alkyl group having from 2 to 10 carbon atoms, an aryl group having from 6 to 15 carbon atoms, or a cycloalkyl group having from 5 to 8 carbon atoms.

7. The process of claim 1, wherein said tertiary amine acid scavenger is tributyl amine.

8. The process of claim 2 wherein said tertiary amine acid scavenger is tributyl amine.

9. The process of claim 3 wherein said tertiary amine acid scavenger is tributyl amine.

10. The process of claim 1 further comprising a washing step to wash the carbamoyl pyridinium compound.

11. The process of claim 10 wherein dichloroethane is used as the washing solvent.

12. The process of claim 10 wherein toluene is used as the washing solvent.

13. The process of claim 4 wherein $R_1$ and $R_2$ together represent pyrrolidine, morpholine, piperidine, piperazine, or 1,2,3,4-tetrahydroquinoline.

14. The process of claim 6 wherein $R_5$, $R_6$ and $R_7$, which are the same or different, each represents an alkyl group having from 3 to 10 carbon atoms.

15. The process of claim 1 wherein the carbamoyl halide is a compound of the formula

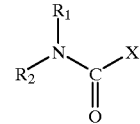

wherein
$R_1$ and $R_2$, which are the same or different, each represents an alkyl group having from 1 to 10 carbon atoms, an aryl group having from 6 to 15 carbon atoms, an aralkyl group having from 7 to 15 carbon atoms, or
$R_1$ and $R_2$ together form a heterocyclic ring, and
X represents a halogen atom,
the pyridine sulfonic acid compound is a compound of the formula

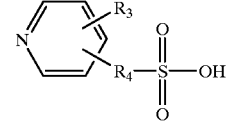

wherein
$R_3$ represents a hydrogen atom, a halogen atom, an alkyl group having from 1 to 10 carbon atoms, an alkoxy group having from 1 to 10 carbon atoms, a carbamoyl group, or an ureido group, and
$R_4$ represents an alkylene group having from 1 to 4 carbon atoms or a single chemical bond between a pyridinium ring and a sulfonic acid moiety,
the tertiary amine acid scavenger is a compound of the formula

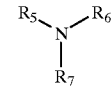

wherein
$R_5$, $R_6$ and $R_7$, which are the same or different, each represents an alkyl group having from 2 to 10 carbon atoms, an aryl group having from 6 to 15 carbon atoms, or a cycloalkyl group having from 5 to 8 carbon atoms.

16. A method for preparing a 1-4(2-sulfoethyl)-hydroxide inner salt comprising the steps of reacting dimethyl carbamoyl chloride with pyridine ethane sulfonic acid in a by-product solubilizing solvent and in the presence of a tertiary amine, producing a reaction mixture comprising the inner salt and a tertiary amine hydrochloride by-product, and separating the inner salt from the reaction mixture, wherein the tertiary amine hydrochloride by-product is substantially soluble in the solvent.

17. A process for preparing a carbamoyl pyridinium compound, which method comprises:
   a) reacting a pyridine sulfonic acid compound with a carbamoyl halide in the presence of an effective amount of a by-product solubilizing solvent and an effective amount of tertiary amine acid scavenger, thereby forming reaction product comprising a carbamoyl pyridinium compound, a tertiary amine hydrohalide by-product and said by-product solubilizing solvent wherein said tertiary amine hydrohalide by-product is substantially soluble in said by-product solubilizing solvent and said carbamoyl pyridinium compound is substantially insoluble in said by-product solubilizing solvent;
   wherein said by-product solubilizing solvent is selected from the group consisting of tetrahydrofuran, methyl-t-butyl ether, 1-methyl-2-pyrrilidinone, dimethylcarbonate, dioxane, anisole, dichloroethane, dichloromethane, ethyl acetate, chlorobenzene, toluene and heptane; and
   b) separating said carbamoyl pyridinium compound from said reaction product.

18. A process for preparing a carbamoyl pyridinium compound, which method comprises:
   a) reacting a pyridine sulfonic acid compound with a carbamoyl halide in the presence of an effective amount of dichloroethane as solvent and an effective amount of tertiary amine acid scavenger, thereby forming reaction product comprising a carbamoyl pyridinium compound, a tertiary amine hydrohalide by-product and said dichloroethane solvent wherein said tertiary amine hydrohalide by-product is substantially soluble in said dichloroethane solvent and said carbamoyl pyridinium compound is substantially insoluble in said dichloroethane solvent; and
   b) separating said carbamoyl pyridinium compound from said reaction product.

19. A process for preparing a carbamoyl pyridinium compound, which method comprises:
   a) reacting a pyridine sulfonic acid compound with a carbamoyl halide in the presence of an effective amount of a by-product solubilizing solvent and an effective amount of tertiary amine acid scavenger, thereby forming reaction product comprising a carbamoyl pyridinium compound, a tertiary amine hydrohalide by-product and said by-product solubilizing solvent wherein said tertiary amine hydrohalide by-product is substantially soluble in said by-product solubilizing solvent and said carbamoyl pyridinium compound is substantially insoluble in said by-product solubilizing solvent;
   b) separating said carbamoyl pyridinium compound from said reaction product; and
   c) washing said carbamoyl pyridinium compound with dichlorethane as solvent.

20. A process for preparing a carbamoyl pyridinium compound, which method comprises:
   a) reacting a pyridine sulfonic acid compound with a carbamoyl halide in the presence of an effective amount of a by-product solubilizing solvent and an effective amount of tertiary amine acid scavenger, thereby forming reaction product comprising a carbamoyl pyridinium compound, a tertiary amine hydrohalide by-product and said by-product solubilizing solvent wherein said tertiary amine hydrohalide by-product is substantially soluble in said by-product solubilizing solvent and said carbamoyl pyridinium compound is substantially insoluble in said by-product solubilizing solvent;
   b) separating said carbamoyl pyridinium compound from said reaction product; and
   c) washing said carbamoyl pyridinium compound with toluene as solvent.

21. A method for preparing a 1-4(2-sulfoethyl)-hydroxide inner salt comprising the steps of reacting dimethyl carbamoyl chloride with pyridine ethane sulfonic acid in dichloroethane as solvent and in the presence of a tertiary amine, producing a reaction mixture comprising the inner salt and a tertiary amine hydrochloride by-product, and separating the inner salt from the reaction mixture, wherein the tertiary amine hydrochloride by-product is substantially soluble in the dichloroethane solvent.

22. A composition comprising:
   a) dichloroethane as solvent;
   b) a carbamoyl pyridinium compound; and
   c) tributylamine hydrohalide;
   wherein b) is substantially insoluble in a), and c) is substantially soluble in a).

23. A composition comprising:
   a) dichloroethane as solvent;
   b) DMC-PES; and
   c) tributylamine hydrohalide;
   wherein b) is substantially insoluble in a), and c) is substantially soluble in a).

24. The process of claim 16, wherein said by-product solubilizing solvent is dichloroethane.

25. The process of claim 16, wherein said tertiary amine is tributyl amine.

* * * * *